United States Patent [19]
Yoshida et al.

[11] Patent Number: 5,122,594
[45] Date of Patent: Jun. 16, 1992

[54] MODIFIED HUMAN PANCREATIC SECRETORY TRYPSIN INHIBITOR

[75] Inventors: Nobuo Yoshida, Nishinomiya; Norihisa Kikuchi, Takatsuki; Masaru Shin, Kobe; Hiroshi Teraoka, Sakai, all of Japan

[73] Assignee: Shionogi & Co., Ltd., Osaka, Japan

[21] Appl. No.: 379,002

[22] Filed: Jul. 12, 1989

[30] Foreign Application Priority Data

Jul. 19, 1988 [JP] Japan ................. 63-181316
Oct. 11, 1988 [JP] Japan ................. 63-255580

[51] Int. Cl.$^5$ .................. C07K 7/10; C12N 15/15
[52] U.S. Cl. ..................... 530/324; 536/27; 435/69.2; 435/320.1; 530/845
[58] Field of Search ............ 530/324, 845; 435/69.2, 435/320.1; 536/27

[56] References Cited

FOREIGN PATENT DOCUMENTS 0264118 4/1988 European Pat. Off. .
63-267289 11/1988 Japan .
2199582A 7/1988 United Kingdom .

OTHER PUBLICATIONS

L. J. Greene et al. Methods Enzymol. vol. 45, 1976, pp. 813–825.
T. Yamamoto et al. Biochemical and Biophysical Research Communications, vol. 132, No. 2, Oct. 30, 1985, pp. 605–612.
M. H. Pubols et al. The Journal of Biological Chemistry, vol. 249, No. 7, Apr. 10, 1974, pp. 2235–2242.
G. Feinstein et al. Eur. J. Biochem. 43, 1974 pp. 569–581.

Primary Examiner—David L. Lacey
Assistant Examiner—Nina Ossanna
Attorney, Agent, or Firm—Morrison & Foerster

[57] ABSTRACT

DNA sequences encoding modified varieties of human PSTI possessing excellent stability in terms of decreased susceptibility to decomposition by proteolytic enzymes such as trypsin, as compared with natural human PSTI, as well as the modified varieties of human PSTI obtained by the expression of the DNA sequences.

4 Claims, 10 Drawing Sheets

```
            1                          10                              20
AspSerLeuGlyArgGluAlaLysCysTyrAsnGluLeuAsnGlyCysThrLysIleTyr
GACTCCCTGGGAAGAGAGGCCAAATGTTACAATGAACTTAATGGATGCACCAAGATATAT
                              30                                      60

30                                     40
AspProValCysGlyThrAspGlyAsnThrTyrProAsnGluCysValLeuCysPheGlu
GACCCTGTCTGTGGGACTGATGGAAATACTTATCCCAATGAATGCGTGTTATGTTTTGAA
                               90                                    120

50
AsnGlnLysArgGlnThrSerIleLeuIleGlnLysSerGlyProCys***
AATCAGAAACGCCAGACTTCTATCCTCATTCAAAAATCTGGGCCTTGCTGA
                              150
```

FIG. I

```
  1                          10                             20
AspSerLeuGlyArgGluAlaLysCysTyrAsnGluLeuAsnGlyCysThrLysIleTyr
GACTCCCTGGGAAGAGAGGCCAAATGTTACAATGAACTTAATGGATGCACCAAGATATAT
                              30                             60

30                             40
AspProValCysGlyThrAspGlyAsnThrTyrProAsnGluCysValLeuCysPheGlu
GACCCTGTCTGTGGGACTGATGGAAATACTTATCCCAATGAATGCGTGTTATGTTTTGAA
                              90                            120

50
AsnArgLysSerGlnThrSerIleLeuIleGlnLysSerGlyProCys***
AATCGGAAAAGCCAGACTTCTATCCTCATTCAAAAATCTGGGCCTTGCTGA
                              150
```

FIG. 2

```
            1                          10                          20
    AspSerLeuGlyArgGluAlaLysCysTyrAsnGluLeuAsnGlyCysThrLysIleTyr
    GACTCCCTGGGAAGAGAGGCCAAATGTTACAATGAACTTAATGGATGCACCAAGATATAT
                       30                                       60

30                          40
    AspProValCysGlyThrAspGlyAsnThrTyrProAsnGluCysValLeuCysPheGlu
    GACCCTGTCTGTGGGACTGATGGAAATACTTATCCCAATGAATGCGTGTTATGTTTTGAA
                       90                                      120

50
    AsnArgLysArgGlnThrSerIleLeuIleGlnLysSerGlyProCys***
    AATCGGAAACGCCAGACTTCTATCCTCATTCAAAAATCTGGGCCTTGCTGA
                              150
```

FIG. 5

```
                              -450        -440        -430
                              GAGCCGAGAGGCAACGCATGGAGGAGCCGG
      -410       -400       -390       -380       -370
ATAATCTGGAGCGGATGGTCTCGATCCTCTCGTTTGTTGCGGTCAGGCTGTTACAGCTCA
      -350       -340       -330       -320       -310
GAGAAAGCTTCACGCTGCCGCAAGCACTCAGGGCGCAAGGGCTGCTAAAGGAAGCGGAAC
      -290       -280       -270       -260       -250
ACGTAGAAAGCCAGTCCGCAGAAACGGTGCTGACCCCGGATGAATGTCAGCTACTGGGCT
      -230       -220       -210       -200       -190
ATCTGGACAAGGGAAAACGCAAGCGCAAAGAGAAAGCAGGTAGCTTGCAGTGGGCTTACA
      -170       -160       -150       -140       -130
TGGCGATAGCTAGACTGGGCGGTTTTATGGACAGCAAGCGAACCGGAATTGCCAGCTGGG
      -110       -100        -90        -80        -70
GCGCCCTCTGGTAAGGTTGGGAAGCCCTGCAAAGTAAACTGGATGGCTTTCTTGCCGCCA
       -50        -40        -30        -20        -10        -1
AGGATCTGATGGCGCAGGGGATCAAGATCTGATCAAGAGACAGGATGAGGATCGTTTCGC 1          10         20         30         40         50         60
ATGATTGAACAAGATGGATTGCACGCAGGTTCTCCGGCCGCTTGGGTGGAGAGGCTATTC
 M  I  E  Q  D  G  L  H  A  G  S  P  A  A  W  V  E  R  L  F
          70         80         90        100        110        120
GGCTATGACTGGGCACAACAGACAATCGGCTGCTCTGATGCCGCCGTGTTCCGGCTGTCA
  G  Y  D  W  A  Q  Q  T  I  G  C  S  D  A  A  V  F  R  L  S
         130        140        150        160        170        180
GCGCAGGGGCGCCCGGTTCTTTTTGTCAAGACCGACCTGTCCGGTGCCCTGAATGAACTG
  A  Q  G  R  P  V  L  F  V  K  T  D  L  S  G  A  L  N  E  L
```

FIG. 6-1

```
             190       200       210       220       230       240
CAGGACGAGGCAGCGCGGCTATCGTGGCTGGCCACGACGGGCGTTCCTTGCGCAGCTGTG
 Q  D  E  A  A  R  L  S  W  L  A  T  T  G  V  P  C  A  A  V 250       260       270       280       290       300
CTCGACGTTGTCACTGAAGCGGGAAGGGACTGGCTGCTATTGGGCGAAGTGCCGGGGCAG
 L  D  V  V  T  E  A  G  R  D  W  L  L  L  G  E  V  P  G  Q 310       320       330       340       350       360
GATCTCCTGTCATCTCACCTTGCTCCTGCCGAGAAAGTATCCATCATGGCTGATGCAATG
 D  L  L  S  S  H  L  A  P  A  E  K  V  S  I  M  A  D  A  M 370       380       390       400       410       420
CGGCGGCTGCATACGCTTGATCCGGCTACCTGCCCATTCGACCACCAAGCGAAACATCGC
 R  R  L  H  T  L  D  P  A  T  C  P  F  D  H  Q  A  K  H  R 430       440       450       460       470       480
ATCGAGCGAGCACGTACTCGGATGGAAGCCGGTCTTGTCGATCAGGATGATCTGGACGAA
 I  E  R  A  R  T  R  M  E  A  G  L  V  D  Q  D  D  L  D  E 490       500       510       520       530       540
GAGCATCAGGGGCTCGCGCCAGCCGAACTGTTCGCCAGGCTCAAGGCGCGCATGCCCGAC
 E  H  Q  G  L  A  P  A  E  L  F  A  R  L  K  A  R  M  P  D 550       560       570       580       590       600
GGCGAGGATCTCGTCGTGACCCATGGCGATGCCTGCTTGCCGAATATCATGGTGGAAAAT
 G  E  D  L  V  V  T  H  G  D  A  C  L  P  N  I  M  V  E  N
```

FIG. 6-2

```
         610       620       630       640       650       660
GGCCGCTTTTCTGGATTCATCGACTGTGGCCGGCTGGGTGTGGCGGACCGCTATCAGGAC
 G  R  F  S  G  F  I  D  C  G  R  L  G  V  A  D  R  Y  Q  D 670       680       690       700       710       720
ATAGCGTTGGCTACCCGTGATATTGCTGAAGAGCTTGGCGGCGAATGGGCTGACCGCTTC
 I  A  L  A  T  R  D  I  A  E  E  L  G  G  E  W  A  D  R  F 730       740       750       760       770       780
CTCGTGCTTTACGGTATCGCCGCTCCCGATTCGCAGCGCATCGCCTTCTATCGCCTTCTT
 L  V  L  Y  G  I  A  A  P  D  S  Q  R  I  A  F  Y  R  L  L 790       800       810       820       830       840
GACGAGTTCTTCTGAGCGGGACTCTGGGGTTCGAAATGACCGACCAAGCGACGCCCAACC
 D  E  F  F  *

850       860       870       880       890       900
TGCCATCACGAGATTTCGATTCCACCGCCGCCTTCTATGAAAGGTTGGGCTTCGGAATCG
         910       920       930       940       950       960
TTTTCCGGGACGCCGGCTGGATGATCCTCCAGCGCGGGGATCTCATGCTGGAGTTCTTCG
         970       980       990      1000      1010      1020
CCCACCCCGGGCTCGATCCCCTCGCGAGTTGGTTCAGCTGCTGCCTGAGGCTGGACGACC
        1030      1040      1050      1060      1070      1080
TCGCGGAGTTCTACCGGCAGTGCAAATCCGTCGGCATCCAGGAAACCAGCAGCGGCTATC
        1090      1100      1110      1120      1130      1140
CGCGCATCCATGCCCCCGAACTGCAGGAGTGGGGAGGCACGATGGCCGCTTTGGTCGACC
        1150
CGGACGGGAC
```

FIG.6-3

```
            1                        10                        20
    MetAspSerLeuGlyArgGluAlaLysCysTyrAsnGluLeuAsnGlyCysThrLysIleTyr
     ←——U-1——→ ←——U-2——→ ←——U-3——→ ←——U-4——→

CGACATGGACTCCCTGGGAAGAGAGGCCAAATGTTACAATGAACTTAATGGATGCACCAAGATATATG
  TGTACCTGAGGGACCCTTCTCTCCGGTTTACAATGTTACTTGAATTACCTACGTGGTTCTATATACTGGGACAGA
     ←————L-1————→ ←————L-2————→ ←————L-3————→ ←————L-4————→

AccI
                        30
AspProValCysGlyThrAspGlyAsnThrTyrProAsnGluCysValLeuCysPhe
     ←——U-5——→ ←——U-6——→ ←——U-7——→

ACCCTGTCTGTGGGACTGATGGAAATACTTATCCCAATGAATGCGTGTTATGTTTT
       CACCCTGACTACCTTTATGAATAGGGTTACTTACGCACAATACAAAACTTTTAGCC
         ←————L-5————→ ←————L-6————→ ←————L-7————→

40                    50
GluAsnArgLysArgGlnThrSerIleLeuIleGlnLysSerGlyProCys***
     ←——U-8——→ ←——U-9——→ ←——U-10——→

GAAAATCGGAAACGCCAGACTTCTATCCTCATTCAAAAATCTGGGCCTTGCTGAG
       TTTGCGGTCTGAAGATAGGAGTAAGTTTTTAGACCCGGAACGACTCCTAG
         ←————L-8————→ ←————L-9————→ ←————L-10————→
                                                    BamHI
```

MODIFIED HUMAN PANCREATIC SECRETORY TRYPSIN INHIBITOR

BACKGROUND OF THE INVENTION

1. Field of the invention:

This invention relates to varieties of modified human PSTI and to DNA sequences encoding the same.

2. Description of the prior art:.

Two types of trypsin inhibitor are known which are derived from the pancreas, i.e., pancreatic secretory trypsin inhibitor (PSTI) and basic pancreatic trypsin inhibitor (BPTI). PSTI is present in all mammals, and is distributed not only in the pancreas but also in the kidney, lung, spleen, liver, brain and other organs. BPTI is distributed in various viscera of cows and other ruminants, but is not present in man or other mammals. Pubols et al. (J. Biol. Chem. 249, 2235, 1974) and Feinstein et al. (Eur. J. Biochem. 43, 569, 1974) have isolated and purified PSTI from human pancreatic juice, and Greene et al. (Methods Enzymol. 45. 813, 1976) determined the structure of this substance. Furthermore, Yamamoto et al. (Biochem. Biophys. Res. Commun. 132, 605, 1985) determined the DNA sequence corresponding to PSTI (FIG. 5). As shown by FIG. 5. human PSTI is a peptide composed of 56 amino acid residues, with a molecular weight of 6,242 daltons. It is known that sulfhydryl groups do not exist in PSTI, since the cysteine residues at positions 9 and 38, as well as 16 and 35, and also 24 and 56 are linked by disulfide bonds.

The trypsin inhibitor described above is present in the acinic cells of the pancreas, and in normal humans is secreted in the pancreatic juice together with various pancreatic enzymes so that it inhibits trypsin in the ductus pancreaticus. However, in acute pancreatitis, for some reason trypsin is activated and then trypsinogen and other enzyme precursors are activated in a chain reaction, and this presumably results in autodigestion of the pancreas. The administration of trypsin inhibitor is effective in the therapeutic treatment of this type of acute pancreatitis. The trypsin inhibitors currently used for this purpose include the above-mentioned bovine pancreatic BPTI as well as synthetic inhibitory agents, etc. In view of its source, human PSTI would appear to be the most appropriate trypsin inhibitor for use in this sort of therapy. However, since this form of PSTI has heretofore been prepared by isolation and purification from human pancreatic juice, sufficiently large quantities for therapeutic use could not be obtained, and therefore up to the present time human PSTI has not been employed in clinical practice. In order to solve this problem of quantitative production, the present inventors have developed a method of obtaining large quantities of human PSTI by applying recombinant DNA techniques (Japanese Laid-Open Patent Publication No. 62-253437). According to this method, human PSTI is expressed as a fusion protein with APH (aminoglycoside 3'-phosphotransferase II). This human PSTI fusion protein can be produced in large quantities in a microbial host, and after cleavage of this fusion protein with cyanogen bromide, human PSTI alone can be isolated and purified. The human PSTI obtained by this method possesses the same amino acid sequence as natural human PSTI, and therefore one may expect the same degree of therapeutic efficacy as that obtainable with natural PSTI in clinical applications. However, PSTI is also a peptide, and therefore with passage of time PSTI is gradually decomposed by proteolytic enzymes such as trypsin. Owing to this shortcoming, in order to achieve an adequately sustained trypsininhibiting effect, the quantity of PSTI which decomposes with passage of time must be monitored and replaced by an equal amount of the fresh substance, which has necessitated troublesome laboratory testing and other additional procedures.

SUMMARY OF THE INVENTION

The inventors have discovered that, by introducing site-specific mutations into the gene which encodes human PSTI, varieties of human PSTI (modified PSTI) with characteristics different from those of the naturally occurring form of PSTI (natural PSTI) can be obtained, and thereby succeeded in completing the present invention.

A modified human PSTI of the present invention, which overcomes the above-discussed and numerous other disadvantages and deficiencies of the prior art, is identical with natural human PSTI except that the arginines at the 42nd and/or 44th positions from the N-terminus of the amino acid sequence of the natural human PSTI are replaced by glutamine and/or serine.

A DNA sequence of the present invention encodes the above-mentioned modified human PSTI derived by replacing the arginines in the number 42 and/or 44 position from the N-terminus of the amino acid sequence of natural human PSTI by glutamine and/or serine.

Another modified human PSTI of the present invention is identical with natural human PSTI except that the arginine at the 42nd or 44th position from the N-terminus of the amino acid sequence of the natural human PSTI is replaced by glutamine or serine, respectively.

Another DNA sequence of the present invention encodes the above-mentioned modified human PSTI derived by replacing the arginine in the number 42 or 44 position from the N-terminus of the amino acid sequence of natural PSTI by glutamine or serine, respectively.

Thus, the invention described herein makes possible the objectives of (1) providing modified varieties of human PSTI; which are more resistant to decomposition by trypsin and other proteolytic enzymes than natural human PSTI and (2) providing DNA sequences which encode modified human PSTI with the advantageous properties stated above by the application of recombinant DNA techniques.

DETAILED DESCRIPTION OF THE INVENTION

The DNA sequences encoding the modified human PSTI of the present invention can be obtained, for example, by using recombinant DNA techniques, specifically, by preparing an expression vector which has the gene encoding natural human PSTI (obtainable by the method described by the inventors in Japanese Laid-Open Patent Publication No. 62-253437) downstream from a suitable promoter, and then introducing a site-specific mutation into the human PSTI gene in this vector. Since the amino acid sequence of human PSTI is comparatively short, the desired variety of modified PSTI can also be obtained by direct chemical synthesis. However, once a recombinant possessing the gene which encodes human PSTI has been prepared, the introduction of a site-specific mutation into this vector to obtain the gene encoding the desired modified PSTI is easily effected, and therefore this method is highly appropriate for the purpose in view. The gene encoding human PSTI has already been cloned from human pancreatic cells by Yamamoto et al. (v.s.), and the DNA sequence of this gene has also been determined. This DNA can also be prepared from human pancreatic cells in accordance with the procedure of Yamamoto et al., but since this sequence is comparatively short, the use of synthetic human PSTI genes is advantageous. The DNA sequence of natural human PSTI is shown in FIG. 5. In the present invention, any DNA sequence encoding the amino acid sequence of human PSTI shown in FIG. 5 can be used. This human PSTI gene is converted into a fusion gene with another gene which possesses highlevel expressive capability under control of a suitable promoter. For example, this can be appropriately accomplished by the formation of a fusion gene with an APH gene in accordance with the method of the above-cited Japanese Laid-Open Patent Publication No. 62-253427. Here, the term APH gene refers to one which contains the structural gene encoding APH (amino-glycoside 3'-phosphotransferase II), and may also contain a promoter, etc. APH genes confer drug resistance against neomycin and kanamycin upon microorganisms.

The base sequence of this APH gene has already been known (Gene, 19, 327, 1982). This base sequence and the amino acid sequence deduced from this base sequence are shown in FIG. 6. A transposon Tn5 and plasmids (e.g., pNEO (Pharmacia)) containing this base sequence are commercially available, and APH genes can be obtained by excision from these element. These APH genes need not contain the complete structural gene for natural APH, and need only encode several amino acids at the N-terminus. For example, one may use the restriction fragment of pNEO (Pharmacia) digested by HindIII and TaqI (containing the APH promoter and the gene encoding the amino acid sequence from the N-terminus to the 82nd amino acid of APH, corresponding to the DNA sequence from the −350 to the 246 position in FIG. 6). Moreover, not only the sequence shown in FIG. 6, but also any modified APH sequence derived from this by substitution, deletion or insertion of some nucleotides can be used.

In order to obtain a gene encoding the modified human PSTI of the present invention, one can, for example, first synthesize the DNA sequence encoding human PSTI. Such a DNA sequence can be synthesized, for example, by synthesizing the 20 types of fragments (U-1 to U-10 and L-1 to L-10) shown in FIG. 7 with the use of an automatic nucleic acid synthesizer, then purifying these products by a chromatographic technique such as high performance liquid chromatography, and after attaching phosphate residues to all these fragments except U-1 and L-10, appropriately joining the fragments with DNA ligases. This type of method is described in Nucleic Acids Res. 13, 2959 (1985). After ligation, the DNA is recovered as usual by phenol extraction and ethanol precipitation, and then fractionated by a conventional method such as polyacrylamide gel electrophoresis. The recovery of the desired DNA fraction from the polyacrylamide gel can be accomplished, for example, by adsorption and elution using a DEAE-C membrane, as described in "Molecular Cloning" (Cold Spring Harbor Laboratory, New York, 1982).

In order to determine the base sequences of the recovered DNA fragments, one may, for example, insert these DNA fragments into an M13 phage vector, use this to transform a suitable host, and then apply screening procedures. M13 phage vectors suitable for this purpose include M13mp10 (manufactured by Takara Shuzo Co.). By cleaving this phage vector with appropriate restriction endonucleases and joining the cleaved vector to the above-mentioned DNA fragments with T4 DNA ligase, one constructs a recombinant phage M13-PSTI, which incorporates DNA encoding human PSTI. This M13-PSTI phage is then introduced into an appropriate host cell. This can be accomplished by, for example, the method described in "Molecular Cloning" (v.s., pp. 250-251). One host cell appropriate for this purpose is *Escherichia coli* K-12 strain JM103. The bacteria into which M13mp10 have been introduced from blue plaques, whereas bacteria transformed by the introduction of M13-PSTI form colorless plaques. If *E. coli* is transfected by the phage DNA obtained from the colorless plaques, this phage DNA proliferates in the bacterial culture, and single-stranded phage DNA is obtained from the supernatant of the culture medium while double-stranded phage DNA can be obtained from the bacterial cell bodies. The single-stranded DNA can be prepared by the method of Messing (Methods Enzymol. 101, 20-28 (1983)). By applying the dideoxy method of base sequencing (Science 214, 1205≅1210 (1981)) to the single-stranded DNA, one can determine whether or not the desired complete structural gene for human PSTI has been inserted. This is a general method, specifically, for example, the commercially marketed M13 Sequencing Kit (manufactured by Takara Shuzo Co.) can be utilized. The preparation of double-stranded DNA from the bacterial cell bodies can be accomplished by using the conventional sodium hydroxide-sodium dodeoylsulfate (SDS) method (Nucleic Acids Res., 7, 1513–1523 (1979)). The double-stranded DNA obtained by this method is used in the construction of expression plasmids.

The PSTI gene is excised from the M13 phage recombinant obtained in this manner, and this gene together with an APH gene excised from the aforementioned pNEO or other vector is inserted into an appropriate plasmid vector, resulting in the desired PSTI expression plasmid. In doing this, the presence of the codon for methionine (i.e., ATG) at the 5' end of the above-mentioned human PSTI gene sequence is desirable. If a gene which encodes a fusion protein with methionine located between the APH and human PSTI moieties is constructed in this manner, then the linkage between the APH and the PSTI can be cleaved by treating the expressed fusion protein with cyanogen bromide, thus facilitating the isolation of human PSTI. The expression plasmid (pUC13-PSTI) can be constructed, for example, by ligating 1) a 180 bp DNA fragment obtained by cleaving the above-mentioned doublestranded DNA with AccI and BamHI, 2) the approximately 2.8 kbp DNA fragment obtained by HindIII-BamHI cleavage of pUC13 and 3) the approximately 600 bp DNA fragment obtained by digestion of pNEO (containing the APH gene of Tn5) with HindIII and TaqI (pUC13-PCTI). In addition to the pUC-13 mentioned in 2) above, other plasmid vectors which can be employed for this construction include pβ-gal13C, pOP203-13, pUC9, pUC8, pEA300, ptrpLI, pBN70, pWTIII, pWT121, pWT131, pKK223-3, pDR540, pDR720, pYEJOOI, pPL-lambda, pKC30, pKC31, pASl, pLC24, pHUB4, pIN-I, pIN-II, pIN-III, pC194, pC221, pUB112, pT127, pSA0503, pE194, etc.; however, the possibilities are not confined to this list; in fact, provided only that the above-described human PSTI and APH fusion gene can be transferred by the vector and expressed in some microorganism, any of the vectors generally employed for transformation by those skilled in genetic engineering can be used for the present purpose. By selecting a vector appropriate for the host, and situating the above-described fusion gene under the control of a suitable promoter, one can construct a recombinant capable of expressing the required APH-human PSTI fusion protein. A promoter for the APH gene is contained in the DNA fragment mentioned in 3) above, obtained by digestion of pNEO; however, this promoter may be changed into another promoter, or the APH gene may placed downstream from an even stronger promoter. The promoters which can be used for the present purpose are the lac, Trp, Tac promoter systems, etc.

The expression plasmid obtained from the above-mentioned DNA fragments 1), 2) and 3) can be introduced into a suitable host and checked for production of PSTI. For example, expression of PSTI as a fusion protein with APH can be verified by transforming suitable host cells through the introduction of the above-mentioned expression plasmid pUC13-PSTI in accordance with the method described in "Molecular Cloning" (v.s.). If host cells such as E. coli (i.e., K-12 strain JM103, C600, AG-1, etc.) or B. subtilis are employed, then PSTI can be produced with high efficiency. Since natural human PSTI has no sugar chains, human PSTI of the same type as the natural form can be produced in prokaryotic cells. The transformed cells are selected for ampicillin resistance. Then, the plasmids contained in these cells are cleaved with HindIII, BamHI and PstI, then analyzed by the sodium hydroxide-SDS method, and the plasmids which are obtained as approximately 3.6 kbp DNA bands are selected. Host cells containing the plasmids selected in this manner are cultured in the presence of ampicillin, the bacterial cell bodies are collected, solubilized and analyzed by SDS-polyacrylamide gel electrophoresis (SDS-PAGE), and the detection of a band corresponding to the PSTI-APH fusion protein, with a molecular weight of 15,000 daltons, verifies that the gene for this fusion protein is indeed being expressed in the host cells.

In order to obtain human PSTI from the fusion protein, since methionine has been inserted between the two proteins as indicated above, human PSTI is easily separated by treatment with cyanogen bromide. Other methods which can ordinarily be employed for this separation include insertion of cysteine between the two proteins and subsequent cleaving with 2-nitro-5-thiocyanobenzoic acid, insertion of asparagine-glycine therebetween and subsequent cleaving with hydroxylamine, insertion of tryptophan therebetween and subsequent cleaving with 2-(2-nitrophenylsulfenyl)-3-methyl-3-bromoindole, insertion of lysine or arginine therebetween and subsequent cleaving with trypsin, insertion of the sequence isoleucine-glutamic acid-glycine-arginine therebetween and subsequent cleaving with blood coagulation factor Xa, etc.; taking the amino acid sequence of human PSTI into consideration, these various methods can be used under appropriate circumstances.

The human PSTI which has been cleaved from the fusion protein can be purified in the usual manner by an appropriate combination of a chromatographic process such as gel filtration chromatography or affinity chromatography, centrifugal separation, etc. Amino acid analysis of the purified PSTI has verified that the amino acid composition of the product is indeed completely identical with that of natural human PSTI (Example 1, Table 1).

Next, in order to obtain the modified human PSTI of the present invention, the expression plasmid pUC13-PSTI described above is used to introduce a site-specific mutation into the PSTI gene. In this manner, one obtains a recombinant possessing DNA which encodes the desired modified human PSTI. This site-specific mutagenesis is effected by an ingenious combination of chemical techniques for DNA synthesis and the enzymatic reactions of DNA replication. To perform this processing, first, one employs chemical methods to synthesize oligonucleotides (short DNA fragments) such that only the base at the target position in the DNA sequence has been altered and the remaining bases are complementary to those of the desired DNA sequence. These DNA fragments are then paired with the DNA which is to undergo mutation (prepared beforehand in single-stranded form). Then, by subjecting these fragments to the action of DNA polymerase, one can synthesize DNA which contains the chemically synthesized oligonucleotides with the altered base sequence and is complementary to the original DNA at all other positions. That is, any DNA molecule with mutations introduced at desired locations can be synthesized in this manner. Specifically, in order to prepare a recombinant possessing DNA which encodes modified human PSTI by the above-described method of site-specific mutagenesis, for example, one first cleaves pUC13-PSTI with restriction endonucleases such as HindIII and BamHI, thus obtaining a fusion gene for human PSTI and APH. This is ligated to the M13 phage vector M13mp10, thereby preparing the recombinant phage M13-APH/PSTI. On the other hand, one also chemically synthesizes the oligonucleotides indicated by the formulae (1) to (3) below, using an automatic nucleic acid synthesizer.

Ser (44)-PSTI

| | 41 | | | 46 | | (1) |
|---|---|---|---|---|---|---|
| 5'-AAT | CGG | AAA | AGC | CAG | ACT T-3' | |
| Asn | Arg | Lys | Ser | Gln | Thr | |

Gln (42)-PSTI

| | 40 | | | 44 | | (2) |
|---|---|---|---|---|---|---|
| 5'-TT | GAA | AAT | CAG | AAA | CGC CA-3' | |
| | Glu | Asn | Gln | Lys | Arg | |

Thr (43)-PSTI

| | 41 | | | 45 | | (3) |
|---|---|---|---|---|---|---|
| 5'-AA | AAT | CGG | ACA | CGC | CAG AC-3' | |
| | Asn | Arg | Thr | Arg | Gln | |

Each of the synthesized oligonucleotides (1) to (3) is then purified by an appropriate combination of chromatographic methods such as gel filtration, high performance liquid chromatography, etc. These purified synthetic oligonucleotides are then phosphorylated and annealed to the above-mentioned recombinant M13-APH/PSTI (which has previously been prepared in single-stranded form). From this annealed hybrid DNA, double-stranded DNA is prepared by using Klenow fragment (Klenow enzyme) and DNA ligase, and the unreacted single-stranded DNA is removed with a nitrocellulose filter, etc. From the double stranded DNA obtained in this manner, one can prepare a recombinant possessing DNA which encodes the modified human PSTI (Ser(44)-PSTI, Gln(42)-PSTI or Thr(43)-PSTI).

By using the dideoxy method to determine the DNA sequence of the modified PSTI gene contained in these recombinants, one may verify that entire sequence of the structural gene for the desired modified human PSTI is included. Employing this method, the inventors have successfully obtained the following DNA sequences (a)-(c).

(a) A DNA sequence identical with that encoding human PSTI except that the guanine residue at the number 125 position from the 5' end has been replaced by adenine (corresponding to a peptide Gln(42)-PSTI derived from PSTI by replacing the arginine at the 42nd position from the N-terminus by glutamine).

(b) A DNA sequence identical with that encoding human PSTI except that the cytosine residue at the number 130 position from the 5' end has been replaced by adenine (corresponding to a peptide Ser(44)-PSTI derived from PSTI by replacing the arginine at the 44th position from the N-terminus by serine).

(c) A DNA sequence identical with that encoding human PSTI except that the adenine residue at the number 128 position from the 5' end has been replaced by cytosine (corresponding to a peptide Thr(43)-PSTI derived from PSTI by replacing the lysine at 43rd position from the N-terminus by threonine).

The base sequences and corresponding amino acid sequences of two of these products, i.e., Gln(42)-PSTI and Ser(44)-PSTI, are shown in FIGS. 1 and 2, respectively.

Next, an expression plasmid is constructed in order to express the modified human PSTI obtained by the above method. To accomplish this, first, the above-described recombinant containing the fusion gene encoding APH and modified human PSTI is treated with the restriction enzymes EcoRI and HindIII, thereby excising the said fusion gene. This DNA fragment is isolated by a method such as polyacrylamide gel electrophoresis and inserted into a suitable plasmid vector. Any of the previously mentioned plasmids used as expression vectors for human PSTI can also be employed for the present purpose, with pUC13 being especially suitable.

The fusion protein of modified human PSTI and APH can be produced by introducing the expression plasmids prepared in this manner into an appropriate microbial host, just as described above with reference to the manufacture of unmodified human PSTI. Thus, since the modified human PSTI protein is expressed in the form of a fusion protein, digestion by the proteases produced by the host microorganism is avoided. The fusion protein obtained by the above procedure is cleaved by one of the appropriate methods stated above, thereby yielding the modified human PSTI. Amino acid analysis of the modified human PSTI so obtained (Ser(44)-PSTI, Thr(43)-PSTI and Gln(42)-PSTI) showed that the numbers of the respective amino acid residues in each of these products differed in the expected manner from those of the original PSTI (Example 2, Table 2). Investigation of the trypsin-inhibiting activity of each variety of modified human PSTI revealed that, in the case of Gln(42)-PSTI and Ser(44)-PSTI, the temporary trypsin inhibition observed in the case of natural human PSTI was diminished, and in fact the persistence of inhibitory effect upon trypsin was actually prolonged as compared with natural human PSTI (Example 2, FIGS. 3 and 4). This demonstrated that the present invention provides modified human PSTI with superior characteristics.

BRIEF DESCRIPTION OF THE DRAWINGS

This invention may be better understood and its numerous objects and advantages will become apparent to those skilled in the art by reference to the accompanying drawings as follows:

FIG. 1 is the amino acid sequence of the modified human PSTI Gln(42)-PSTI of the present invention and the DNA encoding the same.

FIG. 2 is the amino acid sequence of the modified human PSTI Ser(44)-PSTI of the present invention and the DNA encoding the same.

FIG. 5 is the amino acid sequence of natural human PSTI and the DNA encoding the same.

FIG. 6-1, 6-2 and 6-3 show the DNA sequence of the APH gene and the amino acid sequence deduced from this DNA sequence.

FIG. 7 is the DNA sequence of the synthetic human PSTI gene used in the present invention and the amino acid sequence corresponding to this DNA sequence.

DESCRIPTION OF THE PREFERRED EMBODIMENTS

EXAMPLE 1

Figure 3:
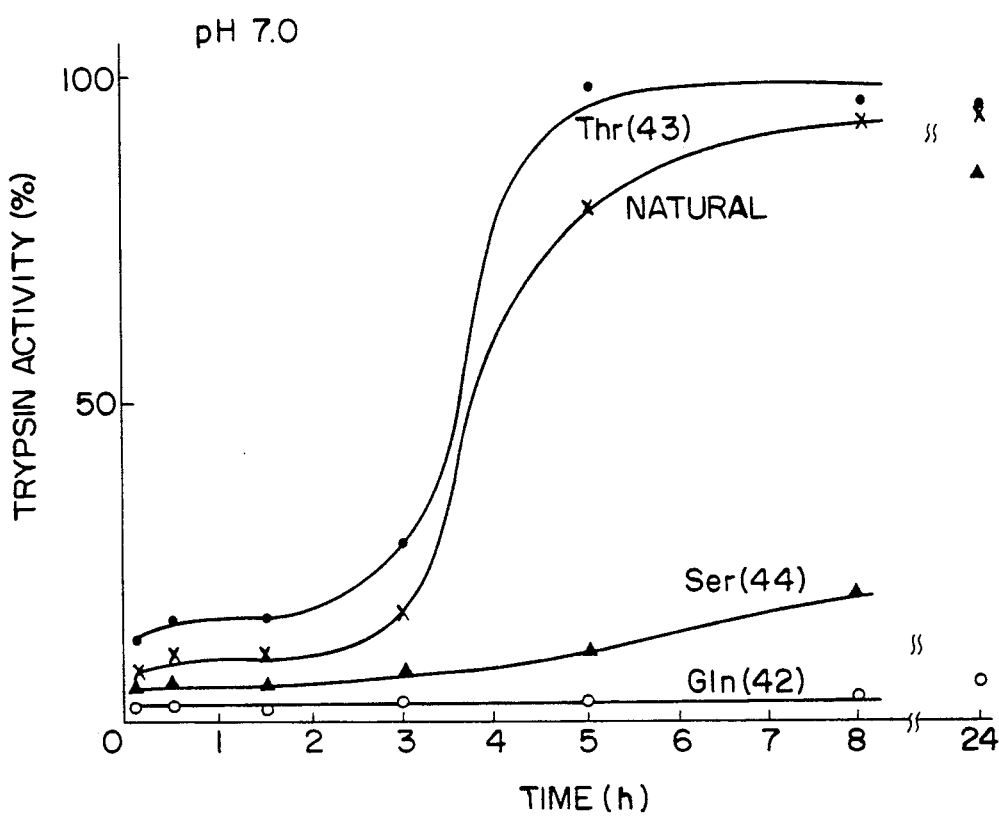
FIG. 3 is of a graph showing the comparative stability under trypsin treatment at pH 7.0 of natural human PSTI and the three varieties of modified human PSTI (viz, Ser(44)-PSTI, Thr(43)-PSTI and Gln(42)-PSTI) of the present invention.

Construction and Expression of DNA Encoding Natural Human PSTI

The DNA sequence of the natural human PSTI gene determined by Yamamoto et al. (Biochem. Biophys. Res. Commun., 132, 605, (1985)) was assumed. The DNA sequence of the structural gene encoding this mature protein of human PSTI was synthesized, the methionine codon ATG was ligated to the 5' end of this sequence, and the termination codon TAG was lligated to the 3' end. Then, this DNA sequence with both start and stop codons was further augmented by additional base sequences in such a manner that the resulting sequence possesses a recognition site for the restriction enzyme AccI at the 5' end as well as a recognition site for the restriction enzyme BamHI at the 3' end, the design being such that a double stranded molecule with single-strands of base length 179 and 181 is formed.

Firstly, in order to prepare the above DNA fragment, the inventors chemically synthesized 20 short-chain DNA fragments comprising two groups, i.e., one group which, if ligated in the proper order, would form a DNA chain including the sequence encoding the amino acid sequence of human PSTI (U-1 to U-10, FIG. 7), and another group which, if suitably ligated, would form the complementary sequence to this DNA chain (L-1 to L-10, FIG. 7). These fragments, if all the varieties are mixed together, can form double stranded structures with mutually complementary fragments joined by hydrogen bonds and having cohesive ends which constitute recognition sites for restriction endonucleases as described above (FIG. 7).

The above 20 varieties of short-chain DNA fragments (U-1 to U-10 and L-1 to L-10) were prepared, using an automatic nucleic acid synthesizer (GENE-TOA-II, manufactured by Nippon Zeon Co.). Each of the fragments so obtained was purified by gel chromatography using Sephadex G-50 and reverse phase high performance liquid chromatography with a silica gel column (Nucleosil 10C18, 10,/μm, 10 ×250 mm).

Since the 20 oligonucleotides synthesized in this manner possess no phosphate group at the 5' terminus, they cannot be joined by T4 DNA ligase as they stand. Therefore using an enzymatic addition reaction, phosphate groups were attached to the 5' termini of eighteen of these twenty varieties of synthetic oligonucleotides, viz, all except U-1 and L-10. This phosphorylation reaction was effected with T4 polynucleotide kinase (manufactured by Takara Shuzo Co.). Approximately 300 pmol of each oligonucleotide was dissolved in 25 μl of the kinase reaction solution (50 mM Tris hydrochloride buffer, 10 mM magnesium chloride, 10 mM 2-mercaptoethanol, app. 1000 pmol ATP, pH 7.6), then the reaction was initiated by adding 3 units of T4 polynucleotide kinase to the solution and continued for 1 hour at 37° C. Then, after heat treatment of the reaction solution at 65° C for 20 minutes to inactivate the T4 polynucleotide kinase, the solution was used directly for the ligation reaction. Then, 50 pmol of each of the eighteen varieties of phosphorylated synthetic oligonucleotides U-2 to U-10 and L-1 to L-9 as well as the two unphosphorylated synthetic oligonucleotides U-1 and L-10 were mixed to prepare a reaction solution for ligation, which was first heat-treated at 80° C for 2 minutes and then slowly cooled down to 20° C. Next, dithiothreitol, ATP and T4 DNA ligase were added, and the ligation reaction was conducted for 5 days at 4° C. The final composition of this ligation reaction solution (200 μl) was 66 mM Tris hydrochloride buffer, 66 mM magnesium chloride, 10 mM dithiothreitol, 1 mM ATP and 700 units T4 DNA ligase (Takara Shuzo Co.). These operations were basically performed in accordance with the procedure described in Nucleic Acids Res. 13, 2959 (1985). After the ligation reaction, phenol extraction and ethanol precipitation were carried out in the usual manner, after which the desired DNA fragment with approximately 180 base pairs was separated by polyacrylamide gel electrophoresis using a Tris borate buffer solution. The DNA fractionated on the gel was stained with ethidium bromide, and a DEAE membrane (Schlleicher and Schuell Co.) was inserted into the gel in the vicinity of the target DNA band. Next, the said DNA was recovered by electrophoretically adsorbing the DNA band onto the DEAE membrane. After the migration of the DNA band toward the DEAE membrane had been completed, the DNA was eluted from the said membrane using a solution containing 1.0 M sodium chloride, 10 mM Tris hydrochloride buffer (pH 8.0) and 1.0 mM EDTA, and recovered from the eluent by ethanol precipitation. The procedure used here is a general one, details of which are described, for example, in "Molecular Cloning" (Cold Spring Harbor Laboratory, New York, 250–251, 1982).

For the purpose of DNA sequencing, the DNA fragments recovered in this manner were inserted into an M13 phage vector. To accomplish this, first, the M13mp10 phage vector (Takara Shuzo Co.) was cleaved with the restriction enzymes AccI and BamHI to form a linear chain, which was then joined, using T4 DNA ligase, to the DNA fragment which had been recovered as described above. The ligation reaction was conducted under virtually the same conditions as the previously described one for ligation of synthetic oligonucleotides, except that the reaction temperature and time in the prevent case were 12° C. and 16 hours, respectively. After ligation, the DNA so treated was used for the transformation of a E. coli host in accordance with the method described in "Molecular Cloning" (Cold Spring Harbor Laboratory, New York, 250–251, 1982).

DNA recipient bacteria obtained from a culture of E. coli K12 strain JMI03 in the logarithmic growth phase by treatment with calcium chloride at 0° C. were mixed with the DNA ligated by the above-described reaction, and the mixture was incubated in ice, after which transformation was effected by heat treatment at 42° C. for 2 minutes. The E. coli cells transfected with the M13mp10 phage were detected as plaques by the following method. First, the JMI03 bacteria were added to a mixture of 20 μl of 100 mM isopropyl-$\beta$-D-thiogalactoside, 50 μl of 2% 5-bromo-4-chloro-3-$\beta$-galactoside, 0.2 ml of a suspension of JM103 in the logarithmic growth phase and 3 ml of soft agar (0.6% liquid agar), and this was poured onto 1.5% agar plates. The agar used here contained TY culture medium (8 g trypton, 5 g yeast extract and 5 g sodium chloride dissolved in 1 liter of water). After overnight incubation at 37° C., the transformed bacteria formed plaques. The bacteria transformed by the M13mp10 phage into which the desired DNA fragments had been inserted (referred to below as M13-PSTI) formed colorless plaques, whereas those bacteria transformed by M13mp10 without the desired DNA insertions formed blue plaques.

Single-stranded phage DNA was prepared from the aforesaid colorless plaques in accordance with the method of Messing (Methods Enzymol. 101, 20–28 (1983)), using the following procedure. 1 ml of a culture solution containing E. coli K-12 strain JM103 incubated for one night was placed in 100 ml of 2xTY medium (viz, 16 g bactotrypton, 10 g yeast extract and 5 g sodium chloride dissolved in 1 liter of water) and shake-cultured for 2 hours at 37° C. This culture solution was divided into 5 ml aliquots, then the agar where the plaques had formed was aspirated into capillary pipettes and inoculated into the said culture solution. Next, the culture solution was incubated for another 5 hours at 37° C. to induce infection by M13-PSTI and release of phage into the culture medium. The intact bacterial cells in the culture solution were used for the preparation of double stranded DNA, while the supernatant of the culture medium, from which the bacterial cells had been removed, was utilized for the preparation of single-stranded phage DNA.

Then, 800μl of 2.5 M sodium chloride solution containing 20% poly-ethylene glycol was added to 4 ml of the culture medium supernatant, and the phage was collected by centrifugal separation. This phage was dissolved in a 500 µl of a solution composed of 10 mM Tris hydrochloride buffer (pH 8.0) and 1 mM ethylenediaminetetraacetic acid (EDTA), after which the single-stranded DNA was recovered by phenol extraction and ethanol precipitation. Replicable double stranded circular DNA was prepared from the phage-infected bacteria in accordance with the conventional sodium hydroxide-sodium dodecyl sulfate (SDS) method (Nucleic Acids Res. 7, 1513-1523 (1979)) by the following procedure. First, the bacterial cells obtained from 5 ml of culture liquid were suspended in 100 µl of 25 mM Tris hydrochloride (pH 8.0, containing 50 mM glucose, 10 mM EDTA and 4 mg/ml lysozyme), and left at room temperature for 5 minutes. To this was added 200µl of 0.2 M sodium hydroxide solution containing 1% SDS, and after gentle mixing the suspension was left in ice for 5 minutes. Then, 150µl of 5 M potassium acetate solution (pH 5.2) was added, and after mixing the suspension was again left in ice for at least 5 minutes. Next, after centrifugation, two volumes of ethanol were added to one volume of the supernatant fluid and the precipitate was recovered. This precipitate was then washed with 70% ethanol, and again recovered by centrifugation. In this manner, replicable double stranded DNA was prepared from the colorless plaques. This DNA was then cleaved at two sites by AccI and BamHI, and formation of DNA fragments with approximately 180 base pairs was verified. Next, the single-stranded phage DNA prepared from the same plaques was used for base sequencing by the dideoxy method (Science 214, 1205-1210 (1981)). Base sequencing was performed with an M13 Sequencing Kit (Takara Shuzo Co.). In this manner, it was verified that the cloned DNA so obtained did indeed include the entire structural gene for the desired PSTI. After verification of the base sequence, the replicable double stranded DNA was used for the construction of a PSTI expression plasmid, as follows.

The PSTI expression plasmid was constructed by joining the following three fragments.

Figure 8:
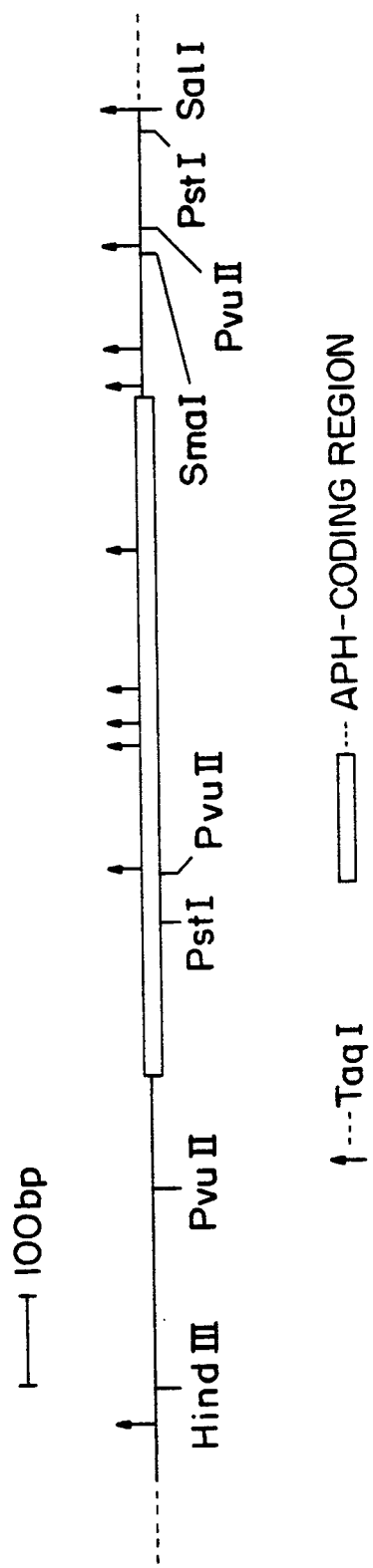
FIG. 8 is a restriction endonuclease map showing the recognition sites of various restriction enzymes within and in the vicinity of the APH gene.
Figure 9:
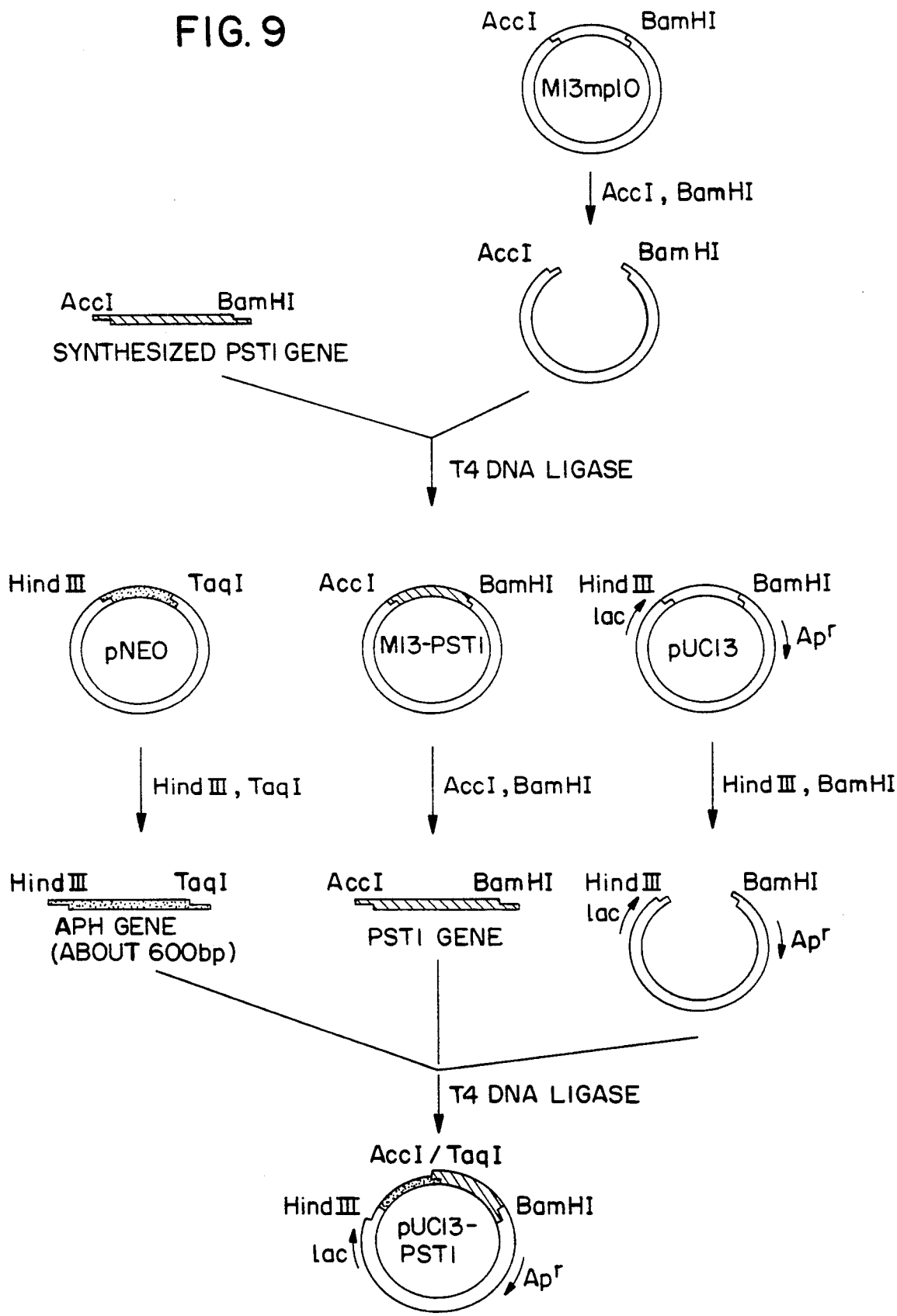
FIG. 9 is an explanatory diagram which schematically indicates the essential features of the procedure for constructing the expression plasmid pUC13-PSTI, containing the DNA sequence encoding the fusion protein of APH and natural human PSTI, which is used in the present invention.

1) The AccI-BamHI fragment of approximately 180 bp with verified base sequence obtained by the above-described ligation reaction of synthetic oligonucleotides.
2) The approximately 2.8 kbp DNA fragment resulting from cleavage of pUC13 (Takara Shuzo Co.) by HindIII and BamHI.
3) The approximately 600 bp DNA fragment obtained by digesting pNEO (containing the APH gene of Tn5; Pharmacia Co.) with HindIII, followed by digestion with TaqI (corresponding to the DNA sequence from position −350 to position 246 in FIG. 6; see FIG. 8).

Among these, the DNA fragments 1) and 3) were separated by polyacrylamide gel electrophoresis, recovered with a DEAE membrane and used for the subsequent ligation reaction. The above-mentioned fragment 2), after verification of cleavage at the two specified sites, was recovered by phenol extraction and ethanol precipitation and then used for the ligation reaction. The PSTI expression plasmid (pUC13-PSTI) obtained by the ligation of these three fragments expresses a fusion protein consisting of PSTI joined at a site 82nd residues downstream from the amino terminus of the APH encoded in the transposon Tn5. As in the case previously described, T4 DNA ligase was employed for the ligation of these three fragments. The DNA obtained by the ligation reaction was used for transformation in accordance with the method described in "Molecular Cloning" (v.s.). Transformation was performed using E. coli K-12 strain C600 or AG-1 that was used as the DNA recipient. Since the transformed bacteria acquire ampicillin resistance, phenotypic selection was performed with reference to the formation of colonies on agar plates containing ampicillin (with LB culture medium, viz, 10 g trypton, 5 g yeast extract and 5 g sodium chloride in 1 liter of water). Using a platinum loop, 12 of the colonies so formed were transplanted to 5 ml of LB culture medium containing 40 µg/ml ampicillin and incubated at 37° C. for 16 hours. Then, the bacteria were collected by centrifugation and the plasmids were analyzed by the previously described sodium hydroxide-SDS method. Since the target plasmid (pUC13-PSTI) contains just one recognition site for each of the restriction enzymes HindIII, BamHI and PstI, this plasmid can be detected by the formation of an approximately 3.6 kb DNA band upon digestion with each of these enzymes.

The clones which were verified as possessing the desired plasmid were cultured in LB medium (containing 40 µg/ml ampicillin) and then stored at −70° C. in the presence of 50% glycerol. Then, 10 µl of this bacterial stock solution was added to 5 ml of LB medium containing ampicillin and incubated at 37° C. for 8 hours. Then, 100 µl of this culture liquid was added to 5 ml of M9 culture medium containing ampicillin (M9 medium was prepared by dissolving 6 g disodium hydrogenphosphate, 3 g potassium dihydrogenphosphate, 0.5 g sodium chloride and 1 g ammonium chloride in 1 liter of water, and after sterilization, adding magnesium sulfate and calcium chloride in quantities such that their final concentrations are 2 mM and 0.1 mM, respectively; in addition, the medium contained 40 µg/ml ampicillin, 0.5% glucose and 0.5% casamino acids), and incubation was continued for 24 hours at 37° C. After the incubation was completed, the bacteria were collected by centrifugation and used for the following analytical procedure.

A small quantity of bacteria was taken as a sample for analysis by sodium dodecyl sulfate-polyacrylamide gel electrophoresis (SDS-PAGE). The bacterial protein was dissolved in a liquid composed of 0.1 M Tris hydrochloride buffer (pH 6.8), 1% SDS, 1% 2-mercaptoethanol and 20% glycerol, extracted and subjected to gel electrophoretic analysis. The fusion protein containing PSTI appeared as a major band at the position corresponding to the expected molecular weight 15,000, thus confirming the expression of this fusion protein in these transformed E. coli. In addition, samples of these transformed E. coli were lysed by methods such as ultrasonication and the protein content of the bacteria was separated into soluble and insoluble fractions by centrifugation; SDS-PAGE analysis of these fractions revealed that the said fusion protein existed mainly in the insoluble protein fraction.

Then, 6 g of these bacteria were suspended in 20 ml of 0.1 M Tris hydrochloride solution (pH 7.0, containing 5 mM EDTA), and centrifuged at 12,000 ×g for 10 minutes. After repeating the same operation, the bacteria were again suspended in 15 ml of 0.1 M Tris hydrochloride solution (pH 7.0, containing 5 mM EDTA, 50 mM benzamidine and 1 mM phenylmethanesulfonyl fluoride (PMSF)), and then crushed three times with a French press at a pressure of 400 kg/sq.cm. Then, 1.05 g of the pellet obtained by 20 minutes of centrifugation at 23,000

×g was dissolved in 10 ml of 0.1 M sodium phosphate (pH 7.0, containing 20 mM dithiothreitol (DTT) and a protein denaturing agent), and this was subjected to gel filtration on a Sephacryl S-200 column (2.6×79 cm), followed by elution with 0.1 M Tris hydrochloride (pH 7.2, containing 1 mM DTT and 7 M urea). The fraction with a molecular weight of approximately 17,000 daltons was collected, dialyzed against distilled water, and lyophilized. To the lyophilate, 2 ml of 70% formic acid solution containing 160 mg of cyanogen bromide was added, and the mixture was allowed to react for 6 hours at room temperature. Then, 18 ml of distilled water was added thereto and the sample was again lyophilized. The lyophilate so obtained was dissolved in 2 ml of 0.5 M Tris hydrochloride (pH 8.1, containing 2 mM EDTA and 6 M guanidine hydrochloride) and 100 μl of 2-mercaptoethanol was added. After reacting for 4 hours at 37° C. under a nitrogen stream, the mixture was dialyzed against distilled water. The sample was then centrifuged at 10,000 × g for 1 minute, to 6 ml of the supernatant fluid so obtained was added 172 mg sodium chloride and 320 μl of 1 M Tris hydrochloride (pH 8.0), and the sample was adsorbed onto an affinity column (2×3 cm) charged with bovine trypsin-CH-Sepharose 4B. This column was then washed successively with 0.05 M Tris hydrochloride (pH 8.0) containing 0.5 M sodium chloride and with distilled water, after which the PSTI was eluted with 10 mM hydrochloric acid, followed by lyophilization, resulting a purified substance of 1.55 mg.

Then, 12 μg of the human PSTI so obtained was placed in test tube (10 × 90 mm), of 4 M methanesulfonic acid (containing 0.2% of 3-(2-aminoethyl)indole) was added, and the sample was hydrolyzed under reduced pressure at 110° C. for 24 hours. This hydrolysate was then subjected to amino acid analysis using a Hitachi Model 835 amino acid analyzer; the results so obtained are given in Table 1, indicating that the amino acid composition of the PSTI obtained by the process described above was completely identical with that of natural PSTI (theoretical values). Also, investigation of the amino acid sequence of the three residues at the N-terminus by the method of Edman (modification of the method of Iwanaga et al., Eur. J. Biochem. 8, 189-199, 1969) revealed that this was Asp-Ser-Leu, i.e., identical with that of natural human PSTI. Moreover, the human PSTI obtained by the present method inhibited bovine trypsin in the stoichiometric molar ratio 1:1, and furthermore, the results of immunological reaction with antibody raised against natural human PSTI (rabbit antiserum polyclonal antibody) were the same as those observed in the case of natural human PSTI (i.e., the behavior of the dilution curve was identical with that of natural human PSTI).

TABLE 1

| Amino acid | Experimental value | Theoretical value |
| --- | --- | --- |
| Asp | 7.8 | 8 |
| Thr | 3.8 | 4 |
| Ser | 2.8 | 3 |
| Glu | 6.2 | 6 |
| Pro | 2.9 | 3 |
| Gly | 5.2 | 5 |
| Ala | 1.4 | 1 |
| ½Cys | 5.6 | 6 |
| Val | 2.0 | 2 |
| Met | 0.0 | 0 |
| Ile | 2.8 | 3 |
| Leu | 4.0 | 4 |

TABLE 1-continued

| Amino acid | Experimental value | Theoretical value |
| --- | --- | --- |
| Tyr | 2.9 | 3 |
| Phe | 1.2 | 1 |
| Lys | 3.8 | 4 |
| His | 0.0 | 0 |
| Trp | 0.0 | 0 |
| Arg | 3.0 | 3 |

EXAMPLE 2

Construction of DNA Sequence Encoding Modified Human PSTI; Expression of Said Modified Human PSTI by Escherichia coli and Purification thereof 1. Preparation of Ser(44)-PSTI Preparation of this modified human PSTI (Ser(44)-PSTI) was effected by preparing, as a template, the single-stranded recombinant M13-APH/PSTI which includes the gene encoding a fusion protein of APH and PSTI, and then introducing thereinto a sitespecific mutation using the synthetic DNA oligomer to be described below as primer. These operations were performed in accordance with the procedure indicated in the manual for the Amersham oligonucleotide-directed in vitro mutagenesis system. a) Preparation of single-stranded DNA containing gene coding for fusion protein of APH and PSTI Bacteria were collected by centrifugation from 5 ml of a liquid LB medium containing a culture of *E. coli* which had been transformed with the PSTI expression plasmid pUC13-PSTI, obtained in the manner described in Example 1, and the said plasmids were recovered by the sodium hydroxide-SDS method. These pUC13-PSTI plasmids were then dissolved in 20 μl of 10 mM Tris hydrochloride (pH 8.0, containing 1 mM EDTA), and were cleaved by a reaction with the restriction enzymes HindIII and BamHI at 37° C. for 1.5 hours. The DNA fragments so obtained were separated by agarose electrophoresis and recovered with a DEAE membrane. Using T4 DNA ligase, these DNA fragments were then spliced to phage M13mp10 which had been cleaved with HindIII and BamHI, thereby constructing a recombinant (M13-APH/PSTI) carrying DNA which encodes the APH-PSTI fusion protein. Using this recombinant, *E. coli* K-12 strain JM103 cells were transformed under the same conditions as those used in Example 1 above, except that the duration of heat treatment at 42° C. after the treatment at 0° C. was done for 1.5 minutes. The JM103 bacteria into which M13-APH/PSTI had been introduced were incubated overnight on agar plates at 37° C. in the same manner as in Example 1, and using 2 ml of this overnight culture liquid, single-stranded DNA was prepared from the bacteria which had formed colorless plaques.

b) Synthesis of primer

The DNA fragment represented by the following base sequence (1) was synthesized with a GENET A-II automatic nucleic acid synthesizer (Nippon Zeon Co.) for use as a primer in site-specific mutagenesis. This DNA fragment includes the sequence encoding the amino acid sequence from the 41st to the 46th residues of the modified human PSTI in which the arginine in position 44 of natural human PSTI has been replaced by serine.

```
                41                    46              (1)
        5'-AAT CGG AAA AGC CAG ACT T-3'
            Asn Arg Lys Ser Gln Thr
```

The DNA fragment so obtained was purified by gel chromatography using Sephadex G-50 and by reverse phase high performance liquid chromatography with silica gel (Nucleosil C18; 10 μm, 10×250 mm).

c) Site-specific mutagenesis in vivo

First, 200 pmol of the DNA fragment (1) purified in above item b) was dissolved in 100 mM Tris hydrochloride buffer solution (pH 7.6, containing 10 mM magnesium chloride, 10 mM DTT and 0.5 mM ATP), and was phosphorylated by a reaction with 10 units of T4 polynucleotide kinase (PL biochemical) at 37° C for 1 hour. Then, the T4 polynucleotide kinase was inactivated by heat treatment at 65° C for 10 minutes. Next, in 17μl of 5-fold diluted Buffer Solution 1 (Amersham), 5 pmol of this phosphorylated DNA fragment was annealed with 1.5 pmol of the single-stranded recombinant (M13-APH/PSTI) obtained in above item a). This reaction was effected by heating for 10 minutes at 70° C. followed by incubation for 30 minutes at 37° C. Then, to this 17μl annealed mixture were added 5 μl of 100 mM magnesium chloride, 19 μl of Nucleotide Mix 1 (Amersham), 6μl of water, 1.6 μl of DNA polymerase I Klenow fragment (3.8 units/μl) and 2.4 μl of T4 DNA ligase (2.5 units/μl), and double stranded DNA was synthesized by allowing this mixture to react overnight (19-21 hours) at 16° C. Next, the residual single-stranded DNA in this mixture, which had not been converted into double strands, was removed by a nitrocellulose filter. Then, 0.1 volumes of 3 M ammonium acetate and 2.5 volumes of ethanol were added to the solution containing the double-stranded DNA, the precipitated DNA was then dissolved in 25 μl of Buffer Solution 2 (Amersham), to 10μl of this solution were added 65μl of Buffer Solution 3 (Amersham) and 0.7μl of restriction enzyme NciI (8 units/μl), and the mixture was allowed to react for 90 minutes at 37° C. Then, to 65.7 μl of this reaction mixture were added 12 μl of 500 mM sodium chloride, of Buffer Solution 4 (Amersham) and of exonuclease III (25 units/μl), and the mixture was allowed to react for 28 minutes at 37° C. This was then heat-treated at 70∞ C. for 15 minutes to terminate the enzymatic reaction. Next, 5μl of 100 mM magnesium chloride, 13μl of Nucleotide Mix 2, 0.86μl of DNA polymerase I (3.5 units/μl) and 0.8 μl of T4 DNA ligase (2.5 units/μl) were added, and a reaction was conducted at 16° C. for 4 hours. In this manner, double stranded DNA containing the gene for Ser(44)-PSTI was prepared, and used for the following transformation.

A DNA recipient obtained by calcium chloride treatment at 0° C. of a culture solution of E. coli K-12 strain JM103 in the logarithmic growth phase was mixed with the above-mentioned double stranded DNA carrying the Ser(44)-PSTI gene. This mixture was incubated at 0° C. for 20 minutes and then heat-treated at 42° C. for 1.5 minutes to effect the transformation of the bacteria.

The JM103 bacteria into which the above-mentioned DNA had been introduced were cultured on agar plates and single-stranded DNA was prepared from the bacteria which produced colorless colonies in the same manner as described in the preceding Example 1. The preparation of replicable double-stranded circular DNA from phage-infected bacteria was also performed by the sodium-hydroxide-SDS method in the same manner as was done in Example 1. That is, the bacteria obtained from 4 ml of culture were suspended in 100μl of 25 mM Tris hydrochloride (pH 8.0, containing 50 mM glucose, 10 mM EDTA and 4 mg/ml lysozyme), and the sample was left at room temperature for 5 minutes. Then, 200 μl of 0.2 M sodium hydroxide containing 1% SDS was added, and after gentle mixing the sample was left in ice for 5 minutes. Next, 150μl of 5 M potassium acetate solution (pH 5.2) was added, and after mixing the sample was left in ice for at least 10 minutes. Then, after centrifuging, replicable double-stranded DNA was recovered from the supernatant by phenol extraction followed by ethanol precipitation. Then, the single-stranded phage DNA prepared from the same plaque was subjected to DNA base sequencing by the dideoxy method, in the same manner as indicated in Example 1 above, and the sequencing results verified that the clone obtained by the present procedure did indeed contain the complete base sequence of the structural gene for the desired modified PSTI (Ser(44)-PSTI). The replicable double-stranded DNA, the base sequence of which had been verified in this manner, was then used for the construction of the following expression plasmid. d) Construction of expression plasmid Approximately 3.5 μg of the replicable double-stranded DNA obtained in above item c) was cleaved with the restriction endonucleases EcoRI and HindIII, and then the EcoRI/HindIII fragment was separated by polyacrylamide gel electrophoresis and recovered with a DEAE membrane. Using T4 ligase, this DNA fragment (containing the gene (approximately 700 bp) encoding the desired APH/Ser(44)-PSTI fusion protein) was ligated with the plasmid pUC13 (Takara Shuzo Co.) which had been cleaved with EcoRI and HindIII, thereby constructing the expression plasmid pUC13-(Ser(44)-PSTI). Using this plasmid, E. coli recipients were transformed by the method indicated in "Molecular Cloning" (v.s.).

e) Expression of Ser(44)-PSTI

Transformation was performed using E. coli K-12 strain C600 or AG-1 as a DNA recipient. Since the transformed bacteria acquire ampicillin resistance, phenotypic selection was performed with reference to formation of colonies on agar plates containing ampicillin (with LB medium, viz, 10 g trypton, 5 g yeast extract and 5 g sodium chloride in 1 liter of water). Using a sterilized bamboo skewer, eight of the colonies so formed were transplanted into 5 ml of LB medium containing 100μg/ml ampicillin which was then incubated 18 hours at 37° C. Then, the bacteria were collected by centrifugation and the plasmids were recovered in the same manner as described in item c) above.

The clones which had been verified as ( possessing the desired plasmid pUC13(Ser(44)-PSTI) were preserved at −70° C. in the presence of 50% glycerol. Then, 0.1 ml of this bacterial stock was added to 100 ml of LB medium containing 100 /μg/ml ampicillin, and this culture was incubated overnight at 37° C.. Next, 37.5 ml of this culture was added to 1.5 liters of LB medium containing 100 μg/ml ampicillin, and this was further incubated for one night at 37° C.. After this incubation was completed, the bacteria were collected by centrifugation and stored at −20° C..

f) Purification of Ser(44)-PSTI 2.2 g of the bacteria obtained in above item d) were suspended in 10 ml of 0.1 M Tris hydrochloride (pH 7.0, containing 5 mM EDTA), and the suspension was centrifuged at 12,000×g for 10 minutes. After repetition of the same operation, the bacteria were suspended in 10 ml of 0.1 M Tris hydrochloride (pH 7.0, containing 50 mM benzamidine and 1 mM PMSF), and this suspension was crushed 3 times under a pressure of 400 kg/sq.cm with a French press. Then, 0.44 g of the pellet obtained by centrifuging this sample for 30 minutes at 23,000×g was dissolved in 10 ml of 0.1 M sodium phosphate (pH 7.0, containing 8 M guanidine hydrochloride and 20 mM DTT), and this was subjected to gel filtration with a Sephacryl S-200 column (2.6×79 cm) and eluted with 0.1 M Tris hydrochloride (pH 7.2, containing 1 mM DTT and 7 M urea). The fraction of molecular weight approximately 17,000 daltons (35 ml), corresponding to the desired APH/PSTI fusion protein, was collected and 20 ml of this fraction was dialyzed against distilled water and then lyophilized. This lyophilate was dissolved in 0.3 ml of 70% formic acid, then 200 μl of cyanogen bromide (200 mg/ml) was added and the mixture was allowed to react at room temperature for 6 hours. Next, 10 times by volume (i.e., 18 ml) of distilled water was added and this mixture was lyophilized. Then, the lyophilate so obtained was dissolved in 2 ml of 0.05 M Tris hydrochloride (pH 8.0, containing 0.5 M sodium chloride) and centrifuged at 10,000×g for 1 minute, and the supernatant was subjected to adsorption in an affinity column (1×3 cm) charged with bovine trypsin-CH-Sepharose 4B. This column was then washed successively with 0.05 M Tris hydrochloride (pH 8.0) and distilled water, after which the modified PSTI was eluted with 12 mM hydrochloric acid and lyophilized to obtain 415 μg of the purified substance.

2. Preparation of Gln(42)-PSTI and Thr(43)-PSTI

Gln(42)-PSTI and Thr(43)-PSTI were prepared in a manner similar to that employed for the preparation of Ser(44)-PSTI, using as primers, however, the synthetic DNA oligomers indicated in the following formulae (2) and (3), respectively.

Gln (42)-PSTI

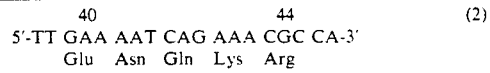

Thr (43)-PSTI

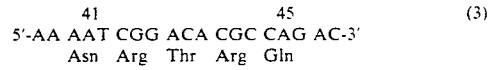

3. Respective properties of three varieties of modified human PSTI a) Amino acid composition With respect to each of the three varieties of modified human PSTI (Ser(44)-PSTI, Gln(42)-PSTI, and Thr(43)-PSTI) described above, approximately 10 μg of the substance was placed in a test tube (10×90 mm), to which was then added 50μl of 4 M methanesulfonic acid (containing 0.2% of 3-(2-aminoethyl)indole), and the mixture was hydrolyzed under reduced pressure for 24 hours at 110° C. This sample was then subjected to amino acid analysis, using a Hitachi Model 835 amino acid analyzer. The amino acid compositions of each variety of modified PSTI as well as the theoretical composition of natural human PSTI are shown in Table 2. As indicated by this table, the numbers of the respective amino acid residues in each of these varieties of modified human PSTI differed from those of the original human PSTI in the theoretically anticipated manner, thereby confirming that the desired varieties of modified human PSTI had indeed been obtained by the processes described above.

TABLE 2

| Amino acid | Gln(42)-PSTI | Thr(43)-PSTI | Ser(44)-PSTI | Natural PSTI (theoretical values) |
|---|---|---|---|---|
| Asp | 7.7(8) | 7.5(8) | 7.8(8) | 8 |
| Thr | 3.8(4) | 4.5(5) | 3.7(4) | 4 |
| Ser | 2.8(3) | 2.7(3) | 3.5(4) | 3 |
| Glu | 7.1(7) | 6.2(6) | 6.4(6) | 6 |
| Pro | 2.8(3) | 2.7(3) | 2.9(3) | 3 |
| Gly | 5.1(5) | 5.0(5) | 4.9(5) | 5 |
| Ala | 1.3(1) | 1.4(1) | 1.3(1) | 1 |
| ½Cys | 5.2(6) | 5.1(6) | 5.0(6) | 6 |
| Val | 2.1(2) | 2.1(2) | 2.0(2) | 2 |
| Met | 0.0(0) | 0.0(0) | 0.0(0) | 0 |
| Ile | 2.9(3) | 2.7(3) | 2.8(3) | 3 |
| Leu | 4.2(4) | 4.0(4) | 4.2(4) | 4 |
| Tyr | 2.9(3) | 2.7(3) | 2.9(3) | 3 |
| Phe | 1.1(1) | 1.3(1) | 1.2(1) | 1 |
| Lys | 4.0(4) | 3.2(3) | 3.8(4) | 4 |
| His | 0.0(0) | 0.0(0) | 0.0(0) | 0 |
| Trp | 0.0(0) | 0.0(0) | 0.0(0) | 0 |
| Arg | 2.2(2) | 3.0(3) | 2.1(2) | 3 |
| Total | 56 | 56 | 56 | 56 |

Trypsin inhibitory activity of modified PSTI

Investigation of the inhibitory activity of each variety of modified PSTI revealed that each of the said varieties of PSTI inhibited human trypsin in the stoichiometric molar ratio of 1:1. Next, the transience of inhibitory effects was investigated with respect to each modified PSTI. This term transience as used here refers to the fact that PSTI initially inhibits human trypsin, but with subsequent passage of time trypsin activity is recovered, indicating that the PSTI has been inactivated. This phenomenon is known to occur in the case of natural PSTI.

First, 1 nmol of human trypsin was incubated at 37° C. in 200μl of 0.1 M Tris hydrochloride (pH 7.0 or 8.0, containing 20 mM calcium chloride and 0.004% Triton X-100) together with 2 nmol of natural human PSTI or one of the three varieties of modified PSTI obtained by the processes described above. At prescribed times a 20 μl aliquot of the mixture was removed and placed in a test tube containing 150μl of 0.5 M Tris hydrochloride (pH 8.0), 200 μl of 5 mM benzoyl-L-arginine p-nitroanilide and 500 μl of distilled water, and incubated at 37° C. for 5 minutes, after which the reaction was terminated by adding 500 μl of 30% acetic acid, then the absorbance at 410 nm was measured and the trypsin-inhibitory activity was calculated. The results of these experiments for pH 7.0 and pH 8.0 are indicated in FIGS. 3 and 4, respectively.

Figure 4:
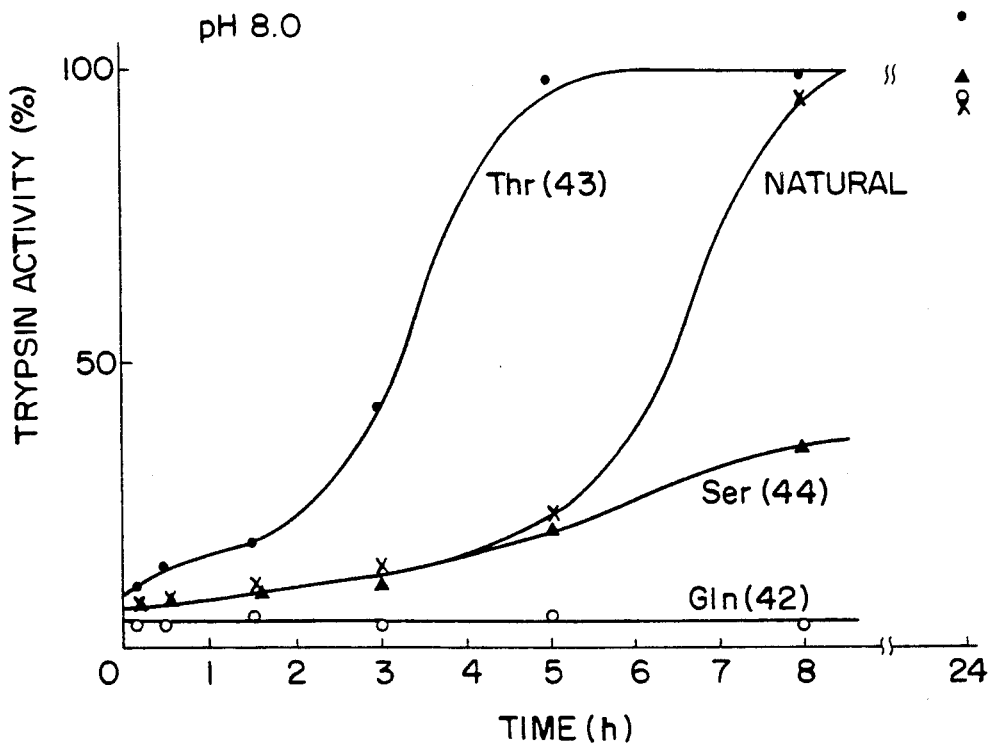
FIG. 4 is of a graph showing the comparative stability under trypsin treatment at pH 8.0 of natural human PSTI and the three varieties of modified human PSTI (viz. Ser(44)-PSTI, Thr(43)-PSTI and Gln(42)-PSTI) of the present invention.

As is clearly shown by FIGS. 3 and 4, for either pH 7.0 and pH 8.0, the temporary inhibitory action was markedly diminished for both Gln(42)-PSTI, with Gln replacing Arg at the 42nd position, and Ser(44)-PSTI, with Ser replacing Arg at the 44th position, as compared with natural human PSTI; thus, the persistence of activity as a trypsin inhibitor was actually increased by these substitutions. In particular, at pH 7.0, Gln(42)-PSTI had maintained trypsin-inhibiting activity even 24 hours after the initiation of the reaction. On the other hand, Thr(43)-PSTI, with Thr replacing Lys at the 43rd position, displayed almost the same inhibitory transience as natural PSTI at pH 7.0, while at pH 8.0 this modified PSTI displayed even less persistence of trysin-inhibiting effect than the natural form.

Thus, the present invention provides DNA sequences encoding modified varieties of human PSTI possessing excellent stability in terms of decreased susceptibility to decomposition by proteolytic enzymes such as trypsin, as compared with natural human PSTI, as well as the modified varieties of human PSTI obtained by expression of the said DNA sequences. Since these modified varieties of human PSTI are produced by recombinant DNA techniques, mass production of these substances at low prices can be realized. Moreover, since the amino acid sequences of these substances differ from that of natural human PSTI only at one position, the clinical application of these substances entails virtually no danger of allergic reactions, as compared with the bovine product BPTI and chemically synthesized agents which have been clinically used as trypsin inhibitors up until now. Furthermore, since the said varieties of modified human PSTI are less susceptible to decomposition by proteolytic enzymes such as trypsin and display more stable and sustained trypsin-inhibiting action as compared with natural human PSTI, these new varieties offer the prospect of higher clinical utility in the treatment of pancreatitis.

It is understood that various other modifications will be apparent to and can be readily made by those skilled in the art without departing from the scope and spirit of this invention. Accordingly, it is not intended that the scope of the claims appended hereto be limited to the description as set forth herein, but rather that the claims be construed as encompassing all the features of patentable novelty that reside in the present invention, including all features that would be treated as equivalents thereof by those skilled in the art to which this invention pertains.

What is claimed is:

1. A modified human pancreatic secretory trypsin inhibitor in which the arginines at the 42nd and/or 44th positions from the N-terminus of the amino acid sequence of natural human pancreatic secretory trypsin inhibitor are replaced by glutamine and/or serine.

2. A DNA sequence encoding the modified human pancreatic secretory trypsin inhibitor set forth in claim 1.

3. A modified human pancreatic secretory trypsin inhibitor in which the arginine at the 42nd or 44th position from the N-terminus of the amino acid sequence of natural human pancreatic secretory trypsin inhibitor is replaced by glutamine or serine, respectively.

4. A DNA sequence encoding the modified human pancreatic secretory trypsin inhibitor set forth in claim 3.

* * * * *